United States Patent

Yanohara

[11] Patent Number: 6,023,884
[45] Date of Patent: Feb. 15, 2000

[54] METHOD FOR EXTERMINATING PESTS INJURIOUS TO PLANTS

[75] Inventor: Yoshitami Yanohara, Osaka, Japan

[73] Assignee: Kabushiki Kaisha Seibutu Kino Kogaku Kenyusho, Osaka, Japan

[21] Appl. No.: 09/118,998

[22] Filed: Jul. 20, 1998

[30] Foreign Application Priority Data

Jul. 29, 1997 [JP] Japan ..................... 9-216945

[51] Int. Cl.$^7$ ................................. A01G 31/00
[52] U.S. Cl. ................................. 47/58.1; 47/59
[58] Field of Search ............... 47/62 A, 62 N, 47/62 R, 58.1, 59, 1.5; 43/137.1

[56] References Cited

U.S. PATENT DOCUMENTS

| | | | |
|---|---|---|---|
| 2,720,727 | 10/1955 | Pidacks | 514/152 |
| 2,855,726 | 10/1958 | Weinstein | 47/58.1 |
| 4,223,477 | 9/1980 | Abernathy | 47/1.5 |

*Primary Examiner*—Michael J. Carone
*Assistant Examiner*—Jeffrey L Gellner
*Attorney, Agent, or Firm*—Nikaido, Marmelstein, Murray & Oram LLP

[57] ABSTRACT

The method for exterminating plants pests comprises making an adjustment for causing the aqueous solution for exterminating pests to have the concentration within the range between the upper limit of being, by 0.4 mol/l, higher than the concentration of the said cell sap of plants and the lower limit of 0 concentration, and dipping the said plants in the said aqueous solution adjusted at the above concentration for a period of time required for exterminating pests.

When the concentration of the said aqueous solution is adjusted within the ranged mentioned above, the pests gathering on the said plants may be suffocated to death without doing any harm to the plants dipped in the said aqueous solution.

2 Claims, 1 Drawing Sheet

METHOD FOR EXTERMINATING PESTS INJURIOUS TO PLANTS

BACKGROUND OF THE INVENTION

The present invention relates to a method for exterminating pests provided with organs for tracheal respiration, such as plant lice, green caterpillars, army worms, etc., which gather on various kinds of plants, such as edible herbs or green or root vegetables, etc. Conventional water culture involves the use of a hydroponic vessel arranged within a spacious cultivation building. The culture solution is put into the hydroponic vessel. The roots of plants are directly immersed in the same culture solution and thereby absorb nutrients. Thus, it becomes unnecessary to use herbicides, soil conditioners, etc. which are used for soil culture. However, many buildings used for water cultivation are open and, therefore, such pests as plant lice, green caterpillars and the like tend to be parasitic on plants. Further, even when the building for cultivation is closed, pests are carried into the building together with seedlings from without.

Thus, there has been, heretofore, used an insecticide or repellent for exterminating such pests. As a result, agricultural chemicals employed remain in the form of residue even in the crop produced by the water culture. Thus, there has arisen a problem to be solved.

OBJECTS AND SUMMARY OF THE INVENTION

Referring to such insects as plant lice, green caterpillars, etc., there are openings called spiracles on their body surface. From these spiracles, finely branched tracheas extend into their body tissue. Oxygen is introduced into the tissue from without by way of these tracheas through spiracles. Then, carbon dioxide is discharged to the outside through spiracles. This is so-called tracheal respiration. Therefore, when insects are kept within the solution for the fixed period of time required, the insects die, because their gaseous exchange through their spiracles becomes impossible. For example, the time required for causing plant lice to die is three to four hours; army worms, 30 minutes to two hours. This fact teaches that, if it is the only purpose to cause pests to die, plants inhabited by pests have only to be dipped for a long time. However, there is a risk that plants themselves may likewise suffer a serious damage if they are carelessly kept in the solution for a long time.

From the standpoint of plant physiology, reference is further made to the aforementioned risk of the plants. When plants are dipped in the aqueous solution, the gaseous exchange of plants through the stomata of their leaves becomes impossible and puts their photosynthesis to an end. But, even if plants stop their photosynthesis, plants may resume their photosynthesis, as long as plant cells have only to continuously live, when they are taken out of the aqueous solution after the immersion for a long period of time. Thus, they may continue to grow in a normal way. This fact is clearly known. In this case, the life or death of plant cells immersed in the aqueous solution is controlled by the osmotic pressure of the aqueous solution. And that the same osmotic pressure is determined by the concentration of the same solution. This is also known. Generally, the osmotic pressure of the plant cell sap varies according to the kind of plants. But it is normally 5 to 10 atm under normal temperature, and the concentration of plant cell sap is 0.2 to 0.8 mol/l. It is, therefore, important how the osmotic pressure and concentration of the aqueous solution should be determined in relation thereto.

In view of the above, when plants are dipped in the aqueous solution which is equal in concentration to the plant cell sap, namely, equal in osmotic pressure to the plant cell sap, there is caused no diffusion of water between the aqueous solution and the plant cells. Thus, the plant cells continue to live, maintaining their shape.

Then, the fact is that, when plants are dipped in the aqueous solution which is lower in concentration than the plant cell sap, namely, lower in osmotic pressure than the plant cell sap, plant cells absorb water, through their semipermeable cell membranes, from the aqueous solution outside and their protoplasm comes to swell within their cells. Incidentally, plant cells are provided with cell walls made of permeable elastic tissue outside of the cell membranes. Because of this fact, the aforementioned swollen protoplasm tends to exert outspreading pressure on the aforementioned cell walls. Due to this action of the protoplasm thereupon, the cell walls extend their pressure to the protoplasm in an attempt to restore their original state. As the cells swell, their concentration therewithin lowers. Then, their osmotic pressure lowers. With their lowering osmotic pressure, the swelling pressure comes to increase. When the wall pressure equal to the swelling pressure comes to be equalized to the osmotic pressure within the cell, the cells automatically stop absorbing water from outside. Then, they continue to live in a swollen and strained state. This phenomenon is also applicable when the plants are immerged in the aqueous solution of 0 concentration, that is to say, water.

Further, in the case where plants are immersed in aqueous solution having a higher concentration than that of a plant cell sap or having the higher osmotic pressure than that of plant cell sap, the water within the cell tends to exude and protoplasm comes to shrink. Finally, plasmolysis is induced. When their plasmolysis is still at an early stage, plasmolyzed cells are restored to their former state or deplasmolyzed when they are immersed in the water again. This is the so-called deplasmolysis. However, when such plasmolysis is further developed, many plants may not be deplasmolyzed and perish.

Thus, the subject for study is, in order to ensure deplasmolysis, to what extent must the concentration of the aqueous solution be allowed to be higher than the concentration of the plant cell sap. Many experiments have been repeated on this subject. As a result, it has been discovered that the allowable upper limit concentration of the same aqueous solution should be, by 0.4 mol/l, higher than the concentration of plant cell sap, though it varies according to the kind of plants involved.

The object of the present invention is to provide a method for thoroughly exterminating pests collecting on plants without using agricultural chemicals.

Another object of the present invention is to provide a method for thoroughly exterminating pests gathering on the plants without having an adverse effect upon the said plants.

Another object of the present invention is to provide a method for exterminating pests on plants under water culture through the ready combating method.

The various objects mentioned above may be realized through the methods of the present invention for exterminating pests. The method for exterminating pests comprises making an adjustment for causing the aqueous solution for exterminating pests to have a concentration within the range between the upper limit of being, by 0.4 mol/l, higher than the concentration of the cell sap of plants from which pests are to be removed and the lower limit of 0 concentration, and immersing and keeping the plants inhabited by pests in the aqueous solution adjusted to have the specified concentration for a period of time required for exterminating the pests.

According to the aforementioned method, the pests collecting on the said plants may be suffocated to death, keeping the cells of the plants alive, by immersing the plants in the aqueous solution, the concentration of which is adjusted within the aforementioned range. Thus, obnoxious pests collecting on plants may be exterminated without using any pesticide and without doing any damage to plants.

Further, as mentioned above, the method for exterminating plant pests gathering on plants under water culture comprises making an adjustment for causing the culture solution for exterminating pests to have the concentration within the range between the upper limit of being, by 0.4 mol/l, higher than the concentration of the cell sap of plants from which pests are to be removed and the lower limit of 0 concentration, and immersing the plants inhabited by pests under water culture in the culture solution the concentration of which is adjusted for a period of time required for exterminating pests.

According to the aforementioned method, the culture solution for water culture is considered the same as the aqueous solution for exterminating pests. Since the plants under water culture are immersed in this culture solution, the work for immersing plants is simplified and labor is saved. Furthermore, the work for returning the said plants to the previous water culture becomes likewise simplified after the extermination of pests.

In addition to the culture solution used for water culture, there are employed water, a solution of salt, a cane sugared water, etc. specially prepared, as "the aqueous solution to be used for exterminating pests", in accordance with the present invention.

DETAILED DESCRIPTION OF THE PREFERRED EMBODIMENTS

EXAMPLE 1

Figure 1:
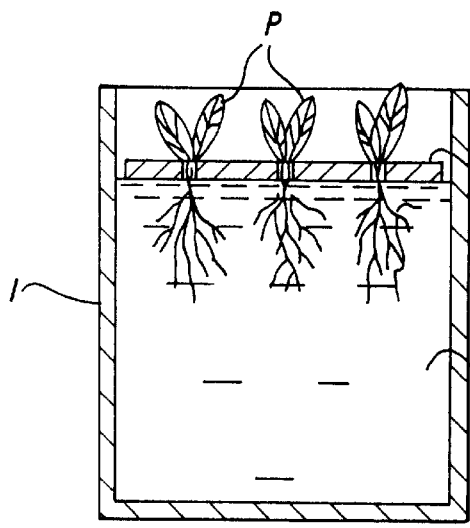
FIG. 1 is a view shown in cross section of the plants under water culture.

As shown in FIG. 1, the culture solution 2 comprising water and various nutrients is put into the box-shaped water culture tank 1 with its top open. The rectangular floatable planting panel 3 made of foamed styrol is caused to float on the surface of the culture solution 2. The root parts of plants P (for example, spinach) are held within penetrating pores made in the said planting panel 3. Their roots are caused to dip in the culture solution 2 under the panel 3.

The concentration of the spinach cell sap is 0.3 mol/l. But the concentration of the culture solution 2 to be used for exterminating pests is adjusted at 0.6 mol/l which is, by 0.3 mol/l, higher than that of the said cell sap.

Figure 2:
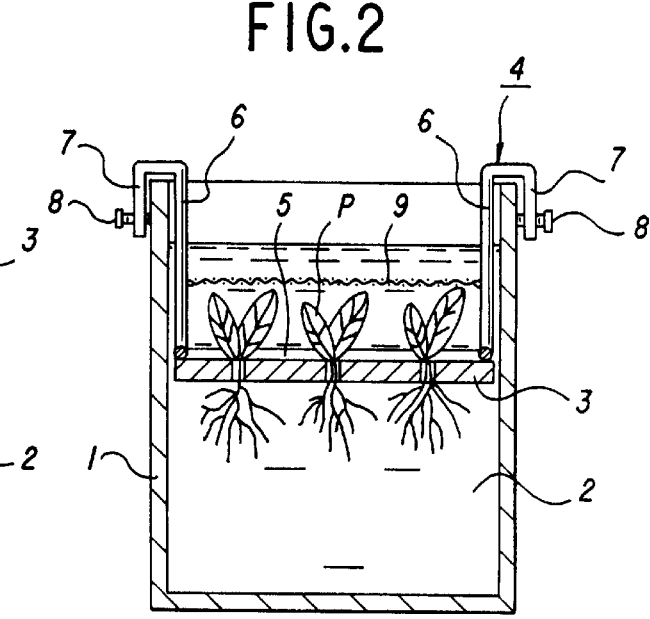
FIG. 2 is a view in cross section of the plants under the treatment for exterminating pests.

In the process of cultivation within the said water culture tank 1, plant lice and green caterpillars collecting on plants P are exterminated in the manner mentioned below. As shown in FIG. 2, the whole planting panel 3 is pushed down by the use of push frame 4 and all plants P are dipped into the culture solution 2.

Figure 3:
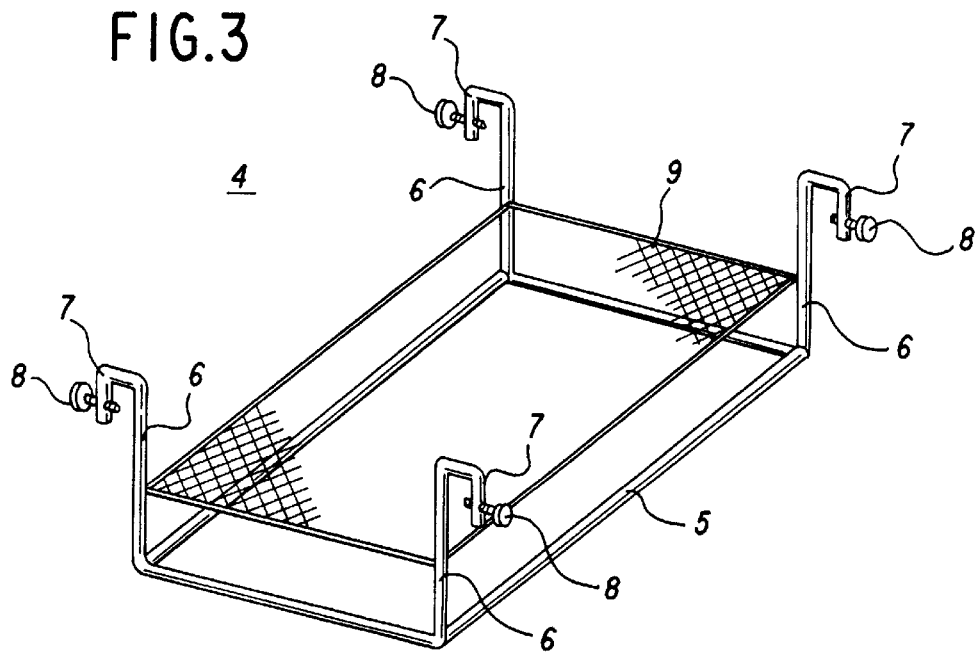
FIG. 3 is a view shown in perspective of the push frame.

Reference is made to the said push frame 4. As shown in FIG. 3, the rectangular frame 5 is made slightly smaller than the said planting panel 3. Arms 6 are projected respectively, at a right angle to the rectangular frame 5, from the four corners of the said frame 5. Simultaneously, the terminal parts of the arms 6 are formed into stoppers 7 bent in a hook shape. The setscrew 8 is screwed on each of stoppers. The net 9 made of metal wire, thread or the like is supported by each of arms 6 in its intermediate part.

In operation, the frame 5 is placed on the four sides of the planting panel 3. Thereafter, each of arms 6 is pushed down, and the plants P are caused to dip into the culture solution 2 together with the planting panel 3. Then, the net 9 prevents the plants from rising to the surface of the solution. While the plants P are allowed to be immersed in the culture solution 2, the setscrews 8 of the stoppers 7 engaged with the side walls of the culture tank 1 are screwed on the said side walls. Thus, the push frame 4 is fixedly placed.

The aforementioned plant immersion was carried out for four hours and ten minutes under the solution temperature of 20° C. in the culture solution 2.

Due to the above immersion, the water within plant cells is gradually diffused to the culture solution 2. In consequence thereof, their protoplasm comes to shrink and finally plasmolysis is induced.

However, the plasmolysis taking place within the plant cells stops at a early stage and no such further noticeable plasmolysis is developed as to cause cells to die out, because the concentration of the culture solution 2 is set at the value, by 0.3 mol/l only, higher than the concentration of the plant cell sap so as to secure the deplasmolysis.

With the start of the said immersion, a part of pests collecting on plants come up, still alive, to the surface of the solution. After they float on the solution for a while, they are suffocated to death and sink in the solution. On the other hand, the remaining pests are, almost out of their tracheal respiration, clinging to the plants in the culture solution. After approximately one hour, green caterpillars are suffocated to death, and separated from plants and sink. After about four hours, plant lice are suffocated to death and follow the same course.

After the extermination treatment, the push frame 4 is lifted and plants P are caused to come up to the surface of the culture solution 2 together with the setting panel 3. Then, the plants are returned to the original water culture status as shown in FIG. 1.

Plants absorb water through their roots from the culture solution for the water culture and supply the same water to each of their cells which are plasmolyzed and remain at the early stage. Thereby, each of these cells is deplasmolyzed and continues to grow in a normal way thereafter.

EXAMPLE 2

In the same manner as shown in FIG. 1, the present example refers to the water culture of lettuces in the same culture tank 1 and setting panel 3. This example shows the extermination of plant lice collecting on lettuces. The culture solution in the culture tank 1 is tentatively transferred to another tank. Instead of this culture solution, water is poured into tank 1 as the aqueous solution of 0 concentration for exterminating pests. In the same manner as the other example, the push frame 4 is used together with the setting panel 3 for immersing the plants into the water.

The immersion was carried out for four hours under the water temperature of 18° C. As a result of the immersion, the plant cells absorb the pest exterminating water and their protoplasm gradually swells. As the cells swell, the concentration and osmotic pressure lower within the cells. Simultaneously, their swelling pressure increases. When the wall pressure equal to the swelling pressure comes to be equalized with the osmotic pressure within the cell, they discontinue to absorb water from outside and do not swell any more. On the other hand, after the immersion for four hours, all plant lice collecting on the plant die and sink.

After the immersion is over, the water within the tank 1 is discharged. And the culture solution kept in the other tank is returned to the tank 1. Then, the water culture is caused to resume its activity. Each plant cell swollen due to the water absorbed during the said immersion gradually returns to its normal condition.

What is claimed is:

1. A method for exterminating pests provided with organs for tracheal respiration on plants in a water culture causing roots of said plants to dip in an aqueous culture solution including a plurality of nutrients, comprising immersing said plants in said aqueous culture solution in which said nutrients have a concentration in a range between an upper limit of 0.4 mol/l higher than the concentration of solutes in cell sap of said plants and a lower limit of zero concentration for a time sufficient to exterminate said pests, thereafter removing said plants from said aqueous culture solution and returning said plants to said original status of said water culture.

2. A method for exterminating plant pests having organs for tracheal respiration on plants comprising immersing said plants in an aqueous treating liquid including at least one solute selected from the group consisting of plant culture solution, salt and cane sugar in an amount up to 0.4 mol/l higher than the concentration of cell sap in said plants for a time sufficient to exterminate said pests and thereafter removing said plants from said aqueous liquid.

* * * * *